(12) United States Patent
Sedaghat-Herati

(10) Patent No.: US 6,462,207 B1
(45) Date of Patent: Oct. 8, 2002

(54) POLYETHYLENE GLYCOL DIENE DERIVATIVES

(75) Inventor: Reza Sedaghat-Herati, Springfield, MO (US)

(73) Assignee: Southwest Missouri State University, Springfield, MO (US)

(*) Notice: Subject to any disclaimer, the term of this patent is extended or adjusted under 35 U.S.C. 154(b) by 0 days.

(21) Appl. No.: 09/661,823

(22) Filed: Sep. 14, 2000

Related U.S. Application Data

(60) Provisional application No. 60/163,212, filed on Nov. 2, 1999, and provisional application No. 60/159,254, filed on Oct. 13, 1999.

(51) Int. Cl.[7] .................. C07D 307/12; C07D 33/02; C07D 43/15
(52) U.S. Cl. .................. 549/429; 549/497; 549/233; 549/234; 568/855; 568/857
(58) Field of Search .................. 568/855, 857; 549/231, 233, 234, 429, 497

(56) References Cited

U.S. PATENT DOCUMENTS

| | | |
|---|---|---|
| 4,002,531 A | 1/1977 | Royer |
| 5,252,714 A | 10/1993 | Harris et al. |
| 5,417,983 A | 5/1995 | Nagase et al. |

OTHER PUBLICATIONS

Alker et al. "[1,4] and [5,5] Thermal Sigmatropic Rearrangements of 2–Pentadienyloxypyridine N–Oxides" J. Chem. Soc. Perkin Trans. 1 (1990) pp. 1637–1643.

Baker et al. "Isolation, Identification and Synthesis of Sex Pheromone Components of the Carob Moth, *Ectomyelois Ceratoniae*" Tetrahedron Letters, vol. 30, No. 22 (1989) pp. 2901–2902.

Chino et al. "Synthesis of a Poly(vinyl ether) Containing a Benzocyclobutene Moiety and Its Reaction with Dienophiles" Journal of Polymer Science: Part A: Polymer Chemistry, vol. 37 (1999) pp. 59–67.

Harris et al. "Assessment of the Effects of Attaching an Enzyme to Glass by a Poly(ethylene glycol) Tether" Journal of Bioactive and Compatible Polymer, vol. 4, No. 3 (1989) pp. 281–295.

Harris et al. "Synthesis of New Poly(Ethylene Glycol) Derivatives" Poly(Ethylene Glycol) Chemistry: Biotechnical and Biomedical Applications, Plenum Press, NY (1992) pp. 371–381.

Herman et al. "Poly(Ethylene Glyol) with Reactive Endgroups: I. Modification of Proteins" Journal of Bioactive and Compatible Polymers, vol. 10, No. 2 (1995) pp. 145–187.

Yoshinga et al. "Effects of Coupling Chemistry on the Activity of Poly(ethylene glycol)–Modified Alkaline Phosphatase" Journal of Bioactive and Compatible Polymers, vol. 4 (1989) pp. 17–24.

Zalipsky "Functionalized Poly(ethylene glycol) for Preparation of Biologically Relevant Conjugates" Bioconjugate Chem., vol. 6, No. 2 (1995) pp. 150–165.

Organic Syntheses Based on Name Reactions and Unnamed Reactions by A. Hassner & C. Stumer. p. 95. reprinted 1995.*

Caplus DN 118:170491 (English abstract) Denchev Z et al 1993 vol. 47 Issue 6, pp. 1019–1026.*

Caplus DN 115:9476 (English Abstract) Denchev Z et al 1991, vol 42, issue 11 pp. 2933–2941.*

* cited by examiner

*Primary Examiner*—Alan L. Rotman
*Assistant Examiner*—Rita Desai
(74) *Attorney, Agent, or Firm*—Senniger, Powers, Leavitt & Roedel

(57) ABSTRACT

A series of polyethylene glycol derivatives possessing a diene moiety has been prepared and characterized. The reactivities of these derivatives in various Diels-Alder reactions have been demonstrated. The potential derivatives, which can be made by various Diels-Alder reactions, are expected to be useful in biotechnical applications.

15 Claims, No Drawings

POLYETHYLENE GLYCOL DIENE DERIVATIVES

REFERENCE TO RELATED APPLICATIONS

This application is a non-provisional application claiming priority from provisional applications serial No. 60/163,212 filed Nov. 2, 1999 and Ser. No. 60/159,254 filed Oct. 13, 1999.

BACKGROUND OF THE INVENTION

This invention relates, in general, to polyethylene glycol ("PEG") derivatives and, in particular, to PEG derivatives containing a diene functionality which may be used in a Diels-Alder reaction to prepare an array of PEG adducts.

PEG is the focus of considerable attention in the biotechnical and biomedical communities. It has been approved by the United States Food and Drug Administration for internal consumption and has been used in a variety of applications including, for example, drug compounding, surface modification (to provide protein and cell rejecting surfaces), hydrogels for cell encapsulation, drug delivery and wound covering, modification of small-molecule pharmaceuticals, and liposomes and micelles for drug delivery. These and other applications for PEG are described in detail in the literature. See, for example, Zalipsky, S., *Bioconjugate Chem.* 6, 150–165 (1995); Herman, et al., Journal of Bioactive and *Compatible Polymers*, 10, 145–187 (1995); *Poly (ethylene glycol) Chemistry. Biomedical and Biotechnical Applications*, J. M. Harris, Editor, Plenum, New York (1992); and *Poly (ethylene glycol) Chemistry and Biological Applications*, J. M. Harris and S. Zalipsky, editors, ACS Symposium Series: American Chemical Society: Washington, D.C. (1997).

For use in these various applications, an "activated" form of PEG, commonly referred to as a PEG derivative is used. Typically, PEG derivatives contain at least one electrophilic center available for reaction with nucleophilic centers of biomolecules (e.g., lysine, cysteine and like residues of proteins) or surfaces (e.g., aminated glass). For example, Royer describes the preparation of PEG acetaldehyde for attaching PEG to enzymes and other proteins in U.S. Pat. No. 4,002,531. Harris et al. describe the preparation of PEG propionaldehyde for linking or tethering molecules to organic or polymer surfaces in water in U.S. Pat. No. 5,252,714. Other PEG derivatives for these and other applications are described in S. Zalipsky, Advanced Drug Delivery Reviews, 16, 157 (1995); K. Nilsson and K. Mosbach, Methods in Enzymology, 104, 56 (1984); C. Delgado, G. E. Francis, and D. Fisher, in "Separations Using Aqueous Phase Systems," D. Fisher and I. A. Sutherland, Eds., Plenum, London, 1989, pp. 211–213; M. B. Stark and J. K. Holmberg, Biotech. Bioeng., 34, 942 (1989); J. M. Harris and K. Yoshinaga, J. Bioact. Compat. Polym., 4, 281 (1989); H. Walter, D. E. Brooks, and D. Fisher (Editors), "Partitioning in Aqueous Two-Phase Systems," Academic Press, Orlando, Fla., 1985; D. Fisher and I. A. Sutherland (Editors), "Separations Using Aqueous Phase Systems: Applications in Cell Biology and Biotechnology," Plenum, London, 1989.

While a number of PEG derivatives have been identified and some are now commercially available, interest remains for new PEG derivatives that possess novel properties. In particular, there is an interest in new PEG derivatives which upon further chemical modification are useful in biomedical applications and permit the synthesis of new polymers (e.g., copolymers, homopolymers, and optically active polymers).

SUMMARY OF THE INVENTION

Among the objects of the present invention, therefore, is the provision of PEG derivatives which upon further chemical modification are useful in biomedical applications, permit the synthesis of new polymers (e.g., copolymers, homopolymers and optically active polymers), are optionally stable in water, selectively react with functional groups such as amines and thiols, are capable of efficiently linking or tethering molecules to organic or polymer surfaces in water by use of PEG derivatives, or may be used as intermediates in the preparation of compositions possessing such properties.

Briefly, therefore, the present invention is directed to a PEG derivative having the formula

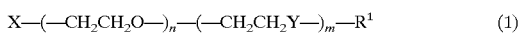

$$X-(-CH_2CH_2O-)_n-(-CH_2CH_2Y-)_m-R^1 \quad (1)$$

wherein m is a cardinal number (that is, 0 or at least 1);

n is at least 1, $R^1$ is a diene moiety selected independently from $R^2$, $R^2$ is a diene moiety selected independently from $R^1$, X is hydroxyl, $-YR^2$, optionally substituted hydrocarbyloxy, or heteroaryloxy; and Y is oxygen, sulfur or $-NH-$.

The present invention is further directed to a process for the preparation of a cyclic product. The process comprises reacting a PEG derivative containing a diene moiety with a dienophile in a Diels-Alder reaction.

Other objects will be in part apparent and in part pointed out hereinafter.

DETAILED DESCRIPTION OF THE PREFERRED EMBODIMENTS

In accordance with the present invention, a class of PEG derivatives having a diene moiety have been discovered which, upon further chemical modification, are of interest in connection with various biotechnical and biomedical applications. In addition, some of these PEG derivatives permit the synthesis of new polymers (e.g., copolymers, homopolymers and optically active polymers).

The PEG derivatives of the present invention have the formula

$$X-(-CH_2CH_2O-)_n-(-CH_2CH_2Y-)_m-R^1 \quad (1)$$

wherein m, n, $R^1$, X and Y are as previously defined. In one embodiment, X is $-YR^2$ and $R^1$ and $R^2$ are the same diene moieties. For example, $R^1$ (and $R^2$ when present) may be a substituted or unsubstituted hydrocarbyl radical containing a conjugated diene. Alternatively, $R^1$ (and $R^2$ when present) may be a substituted or unsubstituted heterocyclic radical. In any event, $R^1$ (and $R^2$ when present) is preferably in, or capable of adopting a cisoid conformation. More preferably, $R^1$ (and $R^2$ when present) is

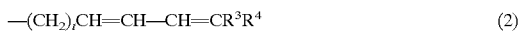

$$-(CH_2)_tCH=CH-CH=CR^3R^4 \quad (2)$$

(3)

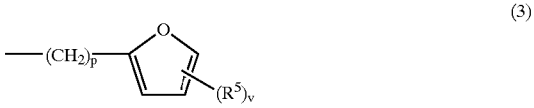

(4)

-continued

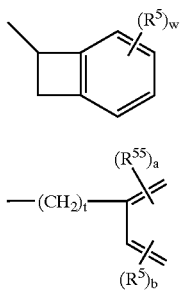

(5)

(6)

wherein
  p is at least 1;
  $R^3$ and $R^4$ are independently hydrogen, alkyl or aryl;
  $R^5$ and $R^{55}$ are independently alkyl, alkenyl, alkynyl, aryl or heteroatomic;
  a is 0–2, preferably 0 or 1, more preferably 0;
  b is 0–2, preferably 0 or 1, more preferably 0;
  t is a natural number greater than zero;
  v is 0–3, preferably 0 or 1, and more preferably 0; and
  w is 0–4, preferably 0 or 1, and more preferably 0.

In one embodiment of the present invention, n is at least about 20, more preferably is at least about 30, and still more preferably about 30 to about 50. In general, it is preferred that n be less than 500, and more preferably less than about 200. In addition, m is preferably no greater than 5, more preferably no greater than 3, and still more preferably 0.

In general, therefore, in preferred PEG derivatives of the present invention n is at least about 20, m is 0–5, X is hydroxyl, alkoxy (such as methoxy) alkenyloxy, alkynyloxy, or aryloxy (such as benzyloxy), Y is oxygen (if m is at least 1), t is 1, and w is preferably 0. In one preferred embodiment of the present invention $R^1$ (and $R^2$ when present) is —$(CH_2)_t$CH=CH—CH=$CR^3R^4$ in the trans configuration, and $R^3$ and $R^4$ are preferably lower alkyl or hydrogen (more preferably hydrogen). In other preferred embodiments, $R^1$ (and $R^2$ when present) corresponds to one of structures 3 to 6, and $R^5$ (if present) or $R^{55}$ (if present) are/is preferably hydrogen or lower alkyl.

The PEG derivatives of the present invention advantageously serve as the diene in a Diels-Alder type cycloaddition reaction with a dienophile. The dienophile for this reaction is preferably a substituted or unsubstituted alkene, alkyne or heteroatomic. In general, dienophiles bearing electron-withdrawing groups such as carbonyl, carboxylate, sulfonyl, sulfonate, cyano, halogen, nitro, trihaloalkyl groups undergo the Diels-Alder reaction with facility. Preferred dienophiles include substituted alkenes such as acrolein, acrylic acid, benzoquinone, maleic anhydride, acrylonitrile, and vinyl ketones such as methylvinyl ketone. Preferred dienophiles also include substituted alkynes such as dicyanoacetylene and esters of acetylenedicarboxylic acid. Heteroatomic dienophiles are also preferred such as the iminourethanes and esters of azodicarboxylic acid.

Diels-Alder reactions are typically carried out in an organic solvent, typically an aprotic organic solvent such as tetrahydrofuran or toluene, or in water at or above room temperature. In general, the reaction is carried out with a molar excess of dienophile with molar ratios of dienophile to diene of about 2:1 being typically preferred.

Definitions

The term "diene moiety" is defined to mean a radical or functional group which enables a compound to react with a dienophile in a Diels-Alder reaction in somewhat the same manner as a conjugated diene reacts with an alkene in a Diels-Alder reaction. Such diene moieties include, for example, conjugated dienes and certain heterocyclic radicals.

The "hydrocarbon" and "hydrocarbyl" moieties described herein are organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbyl groups, and include alkaryl, alkenaryl and alkynaryl. Preferably, these moieties comprise 1 to 20 carbon atoms.

The alkyl groups described herein are preferably lower alkyl containing from one to six carbon atoms in the principal chain and up to 20 carbon atoms. They may be straight, branched chain or cyclic and include methyl, ethyl, propyl, isopropyl, butyl, hexyl and the like. They may be substituted with aliphatic or cyclic hydrocarbyl radicals.

The alkenyl groups described herein are preferably lower alkenyl containing from two to six carbon atoms in the principal chain and up to 20 carbon atoms. They may be straight or branched chain and include ethenyl, propenyl, isopropenyl, butenyl, isobutenyl, hexenyl, and the like. They may be substituted with aliphatic or cyclic hydrocarbyl radicals.

The alkynyl groups described herein are preferably lower alkynyl containing from two to six carbon atoms in the principal chain and up to 20 carbon atoms. They may be straight or branched chain and include ethynyl, propynyl, butynyl, isobutynyl, hexynyl, and the like. They may be substituted with aliphatic or cyclic hydrocarbyl radicals.

The aryl moieties described herein are carbocyclic aromatic moieties, preferably containing from 6 to 20 carbon atoms. They may be substituted with the various hydrocarbyl, substituted hydrocarbyl or heteroatomic moieties defined herein. Phenyl and substituted phenyl are the more preferred aryl.

The heteroatomic moieties described herein are compounds or radicals which contain one atom other than carbon and hydrogen such as nitrogen, and preferably no more than about 20 atoms, usually no more than 5 or 6 atoms. The heteroatomic moiety may be a single atom other than carbon and hydrogen, e.g., a halogen atom, a substituted heteroatom such as hydroxyl or amino, a straight or branched chain containing a heteroatom, or heterocyclic. The heteroatomic moieties may be substituted with hydrogen, hydrocarbyl, heterosubstituted hydrocarbyl or hetero-atom containing substituents with the hetero atoms being selected from the group consisting of nitrogen, oxygen, silicon, sulfur, and halogens. These heteroatomic moieties include hydroxyl; lower alkoxy such as methoxy, ethoxy, butoxy; halogen such as chloro; or fluoro; ethers; esters; heteroaryl such as furyl; alkanoxy; acyl; acyloxy; nitro; amino; and amido.

The heterocyclic moieties described herein are cyclic heteroatomic compounds or radicals, preferably containing a total of 5 to 20 atoms, usually 5 ring atoms, and at least one ring atom other than carbon. The heterocyclic moiety may be heteroaryl, that is, a heterocyclic moiety analogous to the aromatic compounds or radicals, and include, for example, furyl and the like. The heterocyclic moieties may be substituted with hydrocarbyl, heterosubstituted hydrocarbyl or hetero-atom containing substituents with the hetero-atoms being selected from the group consisting of nitrogen, oxygen, silicon, phosphorous, boron, sulfur, and halogens. These substituents include hydroxyl; lower alkoxy such as methoxy, ethoxy, butoxy; halogen such as chloro or fluoro; ethers; acetals; ketals; esters; heteroaryl such as furyl; alkanoxy; acyl; acyloxy; nitro; amino; and amido.

The substituted hydrocarbyl moieties described herein are hydrocarbyl moieties which are substituted with at least one atom other than carbon and hydrogen, including moieties in which a carbon chain atom is substituted with a heteroatom such as nitrogen, oxygen, silicon, phosphorous, boron, sulfur, or a halogen atom. These substituents include hydroxyl; lower alkoxy such as methoxy, ethoxy, butoxy; halogen such as chloro or fluoro; ethers; esters; heteroaryl such as furyl; alkanoxy; acyl; acyloxy; nitro; amino; and amido.

The acyl moieties and the acyloxy moieties described herein contain hydrocarbyl, substituted hydrocarbyl or heteroaryl moieties. In general, they have the formulas —C(O)G and —OC(O)G, respectively, wherein G is substituted or unsubstituted hydrocarbyl, hydrocarbyloxy, hydrocarbylamino, hydrocarbylthio or heteroaryl.

The following Examples are intended to illustrate but not to limit the invention.

EXAMPLE 1

PREPARATION OF METHOXYPOLY (OXYTHYLENE)-(3E)-1,3-PENTADIENE

Synthesis of Methoxyooly(oxyethylene)-(3E)-1,3-pentadiene mPEG-2000 (8.0 g, 4 mmol) in 120 mL of anhydrous THF, under a nitrogen atmosphere was converted to the corresponding alkoxide by dropwise addition of n-butyl lithium (2.5 M in hexane) in the presence of triphenylmethane, as indicator, until the pink color of triphenylmethyl anion persisted. 5-Bromo-(3E)-1,3-pentadiene (1.5 g, 10.2 mmol) was added and the mixture stirred overnight. The mixture was refluxed for three more hours. THF was removed by distillation. The residue was dissolved in water and extracted with $CH_2Cl_2$ and dried over $MgSO_4$. The $CH_2Cl_2$ solution was then added to dry, cold diethyl ether. The precipitated product was collected and dried under vacuum overnight; yield 5.95 g (72%).

Characterization of Methoxypoly(oxyethylene)-(3E)-1,3-pentadiene $^1$H NMR: δ 63.25 (s, 3H, $CH_3O$—), 3.50(s, mPEG backbone), 4.00(dd, 2H, J=1.2 and 6.0 Hz, C5-H), 5.09–5.16 (dm, 1H, J=9.7 Hz, C1-H), 5.19–5.31(dm, 1H, J=16.0 Hz, C1-H), 5.73–5.90(td, 1H, J=6.0 and J=14.4 Hz, C4-H), 6.19–6.48(m, 2H, C2-H and C3-H). GPC analysis of methoxypoly(oxyethylene)-(3E)-1,3-pentadiene indicated a retention volume close to that of mPEG-2000.

In the $^1$H NMR spectrum of methoxypoly(oxyethylene)-(3E)-1,3-pentadiene the following evidence confirmed that the compound being formed was indeed methoxypoly(oxyethylene)-(3E)-1,3-pentadiene. The relative integration of the peaks for the terminal methoxy protons from the mPEG to the dienyl protons was consistent with a 1:1 mPEG to dienyl ratio.

Furthermore, the proton spectrum showed no observable resonance for hydroxyl proton at 4.56 ppm, indicating that substitution was complete.

EXAMPLE 2

PREPARATION OF METHOXYETHOXY-(3E)-1, 3-PENTADIENE

A model compound, methoxyethoxy-(3E)-1,3-pentadiene, was synthesized to facilitate characterization of methoxypoly(oxyethylene)-(3E)-1,3-pentadiene and the product of its reaction with N-phenylmaleimide.

Synthesis of Methoxyethoxy-(3E)-1,3-Pentadiene

Under a nitrogen atmosphere, to a stirred solution of sodium (0.53 g, 23 mmol) in 2-methoxyethanol (50 mL) at room temperature was added 5-bromo-(3E)-1,3-pentadiene (3.38 g, 23 mmol). The mixture was stirred overnight and then refluxed for three more hours. Excess 2-methoxyethanol was removed by distillation. Water was added to the cooled reaction mixture, which was then extracted with diethyl ether. The diethyl ether solution was dried over $MgSO_4$, then stripped off at reduced pressure. Distillation at 87–88° C., 31 mmHg (water aspirator) yielded 2.46 g (75%) of the desired compound.

Characterization of Methoxyethoxy-(3E)-1,3-pentadiene

1H NMR: δ 3.25(s, 3H, $CH_3O$—), 3.47(m, 4H, —$OCH_2CH_2O$—), 4.00(dd, 2H, J=1.2 and 6.0 Hz, C5-H), 5.09–5.16(dm, 1H, J=9.7 Hz, C1-H), 5.19–5.31(dm, 1H, J=16.0 Hz, C1-H), 5.73–5.90(td, 1H, J=6.0 and J=14.4 Hz, C4-H), 6.19–6.48(m, 2H, C2-H and C3-H).

The relative integration of protons on the methoxyethoxy and pentadienyl units are consistent with the proposed structure of Methoxyethoxy-(3E)-1,3-pentadiene, and the coupling constant for protons on C3 and C4 was consistent with a trans configuration (J=14.4 Hz). The $^1$H NMR spectrum also indicated that the resonances at 4.20 ppm due to the methylene protons of 5-bromo-(3E)-1,3-pentadiene had been replaced with a new doublet at 4.00 ppm for the oxymethylene protons attached to the diene moiety.

EXAMPLE 3

DIELS-ALDER REACTIONS WITH N-PHENYLMALEIMIDE

Diels-Alder Reaction of Methoxypoly(oxyethylene)-(3E)-1,3-pentadiene with N-phenylmaleimide A mixture of methoxypoly(oxyethylene)-(3E)-1,3-pentadiene (2.0 g, 0.97 mmol) and N-phenylmaleimide (0.26 g, 1.5 mmol) in benzene (50 mL) was refluxed overnight. The mixture was cooled down and the product was precipitated by addition to dry diethyl ether (300 mL). The product was filtered, washed with diethyl ether, and dried under vacuum (<0.05 mmHg) overnight; yield 1.95 g (90%).

1H NMR: δ 2.18–2.73(overlapping multiplets, 3H, C4-H and 2 C7-H), 3.25(s, 3H, $CH_3O$—), 3.50(s, mPEG backbone), 5.83–6.02(m, 2H, C5-H and C6-H), 7.14–7.52 (m. 5H, Ph). The two diastereotopic hydrogens (centered at 3.72 and 3.84 ppm for the reaction product of methoxyethoxy-(3E)-1,3-pentadiene) were buried under the spinning side bands of the mPEG backbone. The GPC retention volume of the product was very close to that of mPEG-2000.

Diels-Alder Reaction of Methoxyethoxy-(3E)-1,3-pentadiene with N-Phenylmaleimide A mixture of methoxyethoxy-(3E)-1,3-pentadiene (2.3 g, 16 mmol) and N-phenylmaleimide (2.44 g, 14 mmol) in benzene (50 mL) was refluxed overnight. Evaporation of benzene and removal of volatile materials (unreacted methoxyethoxy-(3E)-1,3-pentadiene) under vacuum (<0.05 mmHg) left a slightly yellow viscous liquid; yield 4.19 g (95%).

1H NMR: δ 6 2.18–2.73 (overlapping multiplets, 3H, C4-H and 2 C7-H), 3.25(s, 3H, $CH_3O$—), 3.50(s, mPEG backbone), 5.83–6.02(m, 2H, C5-H and C6-H), 7.14–7.52 (m, 5H, Ph). The two diastereotopic hydrogens (centered at 3.72 and 3.84 ppm) were buried under the spinning side bands of the mPEG backbone. The GPC retention volume of the product was very close to that of mPEG-2000.

EXAMPLE 4

DIELS-ALDER REACTION OF METHOXYPOLY(OXYETHYLENE)-(3E)-1,3-PENTADIENE(1a) WITH MALEIC ANHYDRIDE

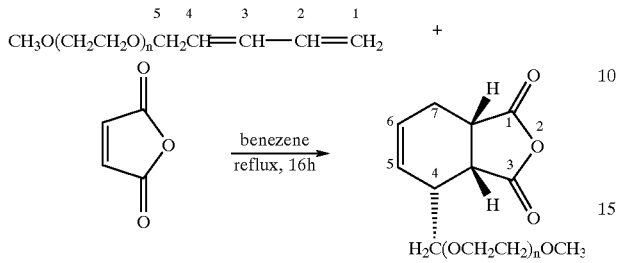

A mixture of Ia(1 g, 0.48 mmol) and maleic anhydride (0.5 g, 5 mmol) in 20 mL of benzene was refluxed overnight. The mixture was cooled and the adduct was precipitated by addition to cold, dry, diethyl ether. The adduct was removed by filtration and dried under vacuum. Yield: 0.9 g. NMR (dmso-$d_6$); δ 2.20–2.75 (overlapping multiplets, 3H, $C_7$—H and $C_4$—H), 3.25 (s, 3H, $CH_3O$), 3.50 (s, PEG backbone), 5.78–6.05 (m 2H, $C_{5-H}$, and $C_{6-H}$). The two diastereotopic hydrogens as well as the protons on $C_{7a}$ and $C_{4a}$ were buried under the spinning side bands of the mPEG backbone.

EXAMPLE 5

DIELS-ALDER REACTION OF METHOXYPOLY(OXYETHYLENE)-(3E)-1,3-PENTADIENE (Ia) WITH ACROLEIN

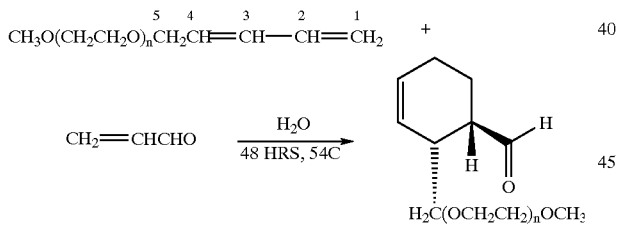

A mixture of Ia(0.5 g, 0.24 mmol) and acrolein(0.75 mL, 11.2 mmol) in 15 mL of water was placed in a water bath at 54C for 24 hrs. More acrolein(0.5 mL, 7.5 mmol) was added and the mixture was placed back in the water bath at 54C for an additional 24 hrs. Excess acrolein was removed by distillation and then the reaction mixture was extracted with methylene chloride. The methylene chloride layer was washed with brine and stored over magnesium sulfate. The adduct was precipitated by addition to cold, dry, diethyl ether. The adduct was removed by filtration and dried under vacuum. Yield: 0.3 g. NMR (dmso-$d_6$); δ 1.50–2.25 (m, 5H, $C_2$—H, $C_5$—H and $C_6$—H) , 3.25 (s, 3H, $CH_3O$), 3.50 (s, PEG backbone), 5.58–5.85 (m, 2H, $C_3$—H and $C_4$—H), 9.65 (s, 1H, CHO). The two diastereotopic hydrogens as well as the proton on $C_1$ were buried under the spinning side bands of the mPEG backbone.

EXAMPLE 6

SYNTHESIS OF mPEG-BENZOCYCLOBUTENYL (IIIa)

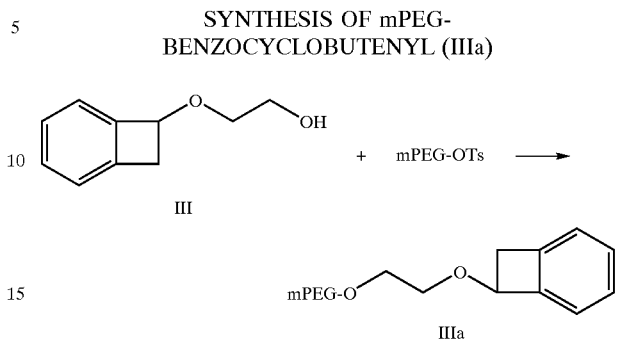

III was prepared by a previously published method [K. Chino, T. Takata, T. Endo, J Polym. Sci.: Part A: Polym. Chem. 37, 59 (1999)]. NaH (0.06 g, 2.5 mmol) was added to a solution of III (0.8 g, 4.9 mmol) in 40 mL of THF. To this solution mPEG-OTs (4 g, 2 mmol) was added and the mixture was stirred at room temperature for 60 hrs. THF was removed by distillation and the residue was dissolved in water and extracted with methylene chloride. The methylene chloride solution was dired over magnesium sulfate and the product was precipitated by addition to cold, dry, diethyl ether. The product was removed by filtration and dried under vacuum. Yield: 3.6 g. NMR(dmso-$d_6$); δ 2.97–3.07(dd, 1H, —CH22—C=), 3.25(s, 3H, CH30—), 3.51(s, mPEG backbone), 5.02–5.09(m, 1H, —O—CH—), 7.17–7.36(m, 4H, Ph). One of the —CH2—C=hydrogens as well as the ethoxy hydrogens are included in the mPEG backbone peak or its spinning side bands.

EXAMPLE 7

REACTION OF IIIa WITH N-PHENYLMALEIMIDE

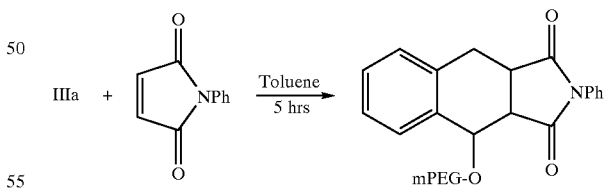

IIIa (0.6 g, 0.3 mmol) and N-phenylmaleimide (0.1 g, 0.6 mmol) and 4-tert-butylcatechol (5 mg, 0.03 mmol) in 30 mL of toluene were refluxed for five hours. The mixture was cooled and the product precipitated by addition to dry diethyl ether. The product was filtered, washed with diethyl ether, and dried under vacuum. Yield: 0.55 g. NMR(dmso-$d_6$); δ 3.25(s, 3H, CH30—), 3.51 (s, mPEG backbone), 4.95–5.00(d, 1H, —O—CH—), 7.22–7.57(m, 9H, Ph).

EXAMPLE 8

SYNTHESIS OF 3-mPEG-FURFURYLMETHANIDE (IV)

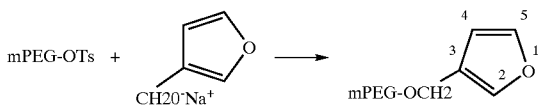

NaH (0.06 g, 2.5 mmol) was added to a solution of 3-furfuryl methanol (1.1 g, 9.2 mmol) in 40 mL of THF. To this solution mPEG-OTs (4.5 g, 2.1 mmol) was added and the mixutre was stirred at room temperature for 60 hrs. THF was removed by distillation and the residue was dissolved in water and extracted with methylene chloride. The methylene chloride solution was dried over magnesium sulfate and the product was precipitated by addition cold, dry, diethyl ether. The product was removed by filtration and dried under vacuum. Yield: 3.5 g. NMR(dmso-$d_6$); δ 3.25(s, 3H, $CH_3O$—), 3.51(S, mPEG backbone), 4.37(s, 2H, —O—$CH_2$—), 6.47(m, 1H, $C_4$—H), 7.6–7.7 (m, 2H, $C_2$—H and $C_5$—H).

EXAMPLE 9

DIELS-ALDER REACTION OF 3-mPEG-FURFURYLMETHANIDE (IV) WITH DIETHYL ACETYLENEDICARBOXYLATE

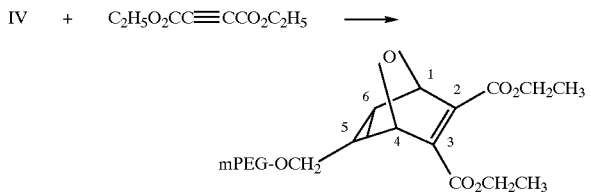

IV(0.8 g, 0.38 mmol) and diethyl acetylenedicarboxylate (0.3 g, 1.8 mmol) in 40 mL of toluene were refluxed for twenty-four hours. The product was precipitated by addition of the cooled reaction mixture to dry diethyl ether. The product was filtered, washed with diethyl ether, and dried under vacuum. Yield: 0.72 g. NMR(dmso-$d_6$); δ 1.25(t, 6H, $CH_3CH_2$—), 3.51(S, mPEG backbone), 4.17(q, 4H, $CH_3CH_2$—), 4.25(s, 2H, —O—$CH_2$C=), 5.6(br s, 1H, $C_1$—H), 5.72 (br s, 1H, $C_4$—H), 6.90(br s, 1H, $C_6$—H).

EXAMPLES 1–9

(GENERAL)

All required reagents were purchased from Aldrich. Methoxypoly(ethylene glycol) (mPEG-2,000) was dried by azeotropic distillation with toluene and then reprecipitated by dropwise addition to cold, dry diethyl ether. 2-Methoxyethanol (anhydrous), and DMSO-$d_6$ were used without further purification. 5-Bromo-(3E)-1,3-pentadiene was prepared by methods previously published. Alker, D.; Olis, W. D.; Shahriari-Zavarah, H. J.; Chem. Soc. Perkin Trans. 1, 1990, 1637. Baker, T. C.; Francke, W.; Löfstedt, C.; Hansson, B. S.; Du, J. -W.; Phelan, P. L.; Vetter, R. S.; Youngman, R.; Tetrahedron Letters 1989, 30, 2901. The above bromide can also be prepared by reaction of 3-hydroxy-1,4-pentadiene with $PBr_3$. However, this method yields a mixture of cis and trans isomers (more than 90% trans isomer). C. P. Reghunadhan Nair, P. Chaumont, and D. Charmot, J. Polym. Science: Part A: Polymer Chemistry, 33, 2773 (1995). N-phenylmaleimide was recrystallized from ethanol/water mixture(1:2 by volume).

1H NMR spectra were recorded at room temperature on a Varian Gemini-200 spectrometer operating at 200 MHZ. The NMR solvent was DMSO-$d_6$ in all cases. Chemical shifts are referenced to internal TMS and reported in ppm. Gel permeation chromatography (GPC) analysis was performed on a Waters liquid chromatograph system using Styragel columns, and a differential refractomoter with tetrahydrofuran (THF) as eluent.

As various changes could be made in the above compositions and processes without departing from the scope of the invention, it is intended that all matter contained in the above description be interpreted as illustrative and not in a limiting sense.

What is claimed is:

1. A compound having the formula:

wherein n is at least 20;

$R^1$ is —$(CH_2)_t$CH=CH—CH=$CR^3R^4$;

$R^2$ is a diene moiety selected independently from $R^1$;

$R^3$ and $R^4$ are independently hydrogen, alkyl or aryl;

t is a natural number greater than zero;

X is hydroxyl, —$YR^2$, optionally substituted hydrocarbyloxy, or heteroaryloxy; and Y is oxygen, sulfur or —NH—.

2. The compound of claim 1 wherein X is hydroxyl, alkoxy, alkenoxy, alkynyloxy or benzyloxy.

3. The compound of claim 1 wherein $R^3$ and $R^4$ are hydrogen.

4. The compound of claim 3 wherein t is 1.

5. The compound of claim 3 wherein X is hydroxyl, hydrocarbyloxy or heteroaryloxy.

6. The compound of claim 1 wherein X is hydroxyl, hydrocarbyloxy or heteroaryloxy.

7. A process for the preparation of a cyclic reaction product, the process comprising reacting a polyethylene glycol derivative containing a diene moiety with a dienophile in a Diels-Alder reaction wherein the polyethylene glycol derivative corresponds to the compound of claim 1.

8. The process of claim 7 wherein X is hydroxyl, alkoxy or benzyloxy.

9. The process of claim 7 wherein $R^3$ and $R^4$ are hydrogen.

10. The process of claim 9 wherein t is 1.

11. The process of claim 10 wherein the dienophile is a substituted alkene, a substituted alkyne or a heteroatomic dienophile.

12. The process of claim 7 wherein the dienophile is acrolein, acrylic acid, benzoquinone, maleic anhydride, acrylonitrile, or a vinyl ketone.

13. The process of claim 7 wherein the dienophile is dicyanoacetylene or an ester of acetylenedicarboxylic acid.

14. The process of claim 7 wherein the dienophile is an iminourethane or an ester of azodicarboxylic acid.

15. The process of claim 9 wherein X is hydroxyl, alkoxy or benzyloxy.

* * * * *